United States Patent [19]

Yamaguchi et al.

[11] Patent Number: 4,701,558

[45] Date of Patent: Oct. 20, 1987

[54] METHOD FOR PURIFYING AQUEOUS ACRYLAMIDE SOLUTION

[75] Inventors: Yasumasa Yamaguchi; Masashi Nishida, both of Kanagawa, Japan

[73] Assignee: Nitto Chemical Industry Co., Ltd., Tokyo, Japan

[21] Appl. No.: 799,051

[22] Filed: Nov. 18, 1985

[30] Foreign Application Priority Data

Nov. 16, 1984 [JP] Japan ................................ 59-240846

[51] Int. Cl.$^4$ ...................... C07C 102/08; C12P 13/02
[52] U.S. Cl. .................................... 564/127; 435/129; 564/128; 564/206
[58] Field of Search ............... 564/128, 131, 206, 127; 435/129

[56] References Cited

U.S. PATENT DOCUMENTS

| | | | |
|---|---|---|---|
| 3,923,741 | 12/1975 | Asano et al. | 564/127 X |
| 3,941,837 | 3/1976 | Asano et al. | 564/127 |
| 4,001,081 | 1/1977 | Commeyras et al. | 435/129 |
| 4,248,968 | 2/1981 | Watanabe et al. | 435/227 X |

*Primary Examiner*—Charles F. Warren
*Assistant Examiner*—Carolyn S. Greason
*Attorney, Agent, or Firm*—Sughrue, Mion, Zinn, Macpeak and Seas

[57] ABSTRACT

A method for purifying an aqueous acrylamide solution by using activated carbon is disclosed. The method comprises contacting activated carbon with water having oxygen dissolved therein until the dissolved oxygen concentration in water after the contact increases to at least 0.5 ppm, and then contacting the aqueous acrylamide solution with the thus treated activated carbon. The method can prevent polymerization of acrylamide around activated carbon, and the resulting purified aqueous acrylamide solution requires no further purification, such as ion-exchanging.

15 Claims, No Drawings

METHOD FOR PURIFYING AQUEOUS ACRYLAMIDE SOLUTION

FIELD OF THE INVENTION

This invention relates to a method for purifying an aqueous acrylamide solution, and more particularly to a method for purifying an aqueous acrylamide solution with activated carbon that has been subjected to a specific treatment.

BACKGROUND OF THE INVENTION

Acrylamide has hitherto been prepared by a so-called catalytic hydration process which comprises reacting acrylonitrile with water in the presence of a catalyst, such as a copper catalyst.

An aqueous acrylamide solution prepared by the catalytic hydration process tends to undergo coloration or become turbid immediately after the preparation thereof, or with the passage of time, due to trace amounts of impurities, such as decomposition products of a stabilizer present in the starting acrylonitrile, substances eluted from the catalyst used, by-products, and the like.

The crude aqueous acrylamide solution containing such impurities should be subjected to a purification step to remove the color or turbidity before it is commercially presented in the form of an aqueous solution or crystals. It has been generally considered preferable to carry the purification by passing the aqueous solution through a column packed with activated carbon, particularly granular activated carbon. However, acrylamide is very apt to be polymerized around activated carbon, thus causing obstruction of the column. As a result, the advantages of the granular activated carbon cannot be fully utilized. In an attempt to prevent polymerization of acrylamide, a method has been proposed of incorporating cupric ion in the activated carbon in advance, as disclosed in Japanese Patent Publication No. 28608/76 (corresponding to U.S. Pat. No. 3,923,741).

In recent years, a process for preparing acrylamide by direct hydration of acrylonitrile using microorganisms capable of hydrating nitriles has been proposed, as described, e.g., in Japanese patent application Ser. No. (OPI) 86186/76 (corresponding to U.S. Pat. No. 4,001,081) and Japanese Patent Publication No. 17918/81 (corresponding to U.S. Pat. No. 4,248,968) (the term "OPI" used herein means an "unexamined published application"). According to this microbiological process, if the acrylamide concentration is increased, pigments and traces of impurities tend to be extracted from the microorganism to enter into the aqueous solution. Therefore, it is desirable to purify the aqueous solution obtained by this process by treating with activated carbon similarly as in the case of the aforesaid catalytic hydration process.

However, when the acrylamide aqueous solution obtained by the microbiological process is purified using activated carbon in which cupric ion has been incorporated for the purpose of preventing polymerization of acrylamide in accordance with the conventional technique, the cupric ion tends to be extracted into the aqueous solution, resulting in not only reduction of cupric ions adsorbed on the activated carbon to readily cause polymerization of acrylamide around the activated carbon, but also incorporation of cupric ions that were not formerly present in the crude aqueous solution in the purified solution. The extraction or dissolution of cupric ions in the acrylamide aqueous solution is believed related to a copper ion equilibrium between activated carbon and the aqueous solution. An aqueous acrylamide solution containing a cupric ion even in a trace amount is unsuitable as a monomer for obtaining high molecular weight polymers, and is, therefore, required to be further purified by ion-exchange resins.

SUMMARY OF THE INVENTION

Accordingly, an object of this invention is to provide a method of purifying an aqueous acrylamide solution by using activated carbon, which can prevent polymerization of acrylamide around activated carbon without requiring any further purification procedure with ion-exchange resins.

Thus, the present invention is directed to a method for purifying an aqueous acrylamide solution by using activated carbon, which comprises contacting activated carbon with water having oxygen dissolved therein until the dissolved oxygen concentration in the effluent water that has been contacted with the activated carbon increases to at least 0.5 ppm, and then contacting the aqueous acrylamide solution with the thus treated activated carbon.

DETAILED DESCRIPTION OF THE INVENTION

In the present invention, it is necessary to contact the activated carbon to be used with water containing dissolved oxygen until the resulting water after contact has a dissolved oxygen concentration of not less than 0.5 ppm, and preferably not less than 1 ppm.

Contact between activated carbon and water containing dissolved oxygen can usually be carried out by passing water containing dissolved oxygen through a packed bed, e.g., a column, packed with activated carbon. In this case, after the concentration of dissolved oxygen in the effluent water reaches at least 0.5 ppm, an aqueous acrylamide solution can be fed to the activated carbon-packed bed.

Water to be fed to activated carbon should have a dissolved oxygen concentration of at least 1 ppm, and preferably 3 ppm or more. When water having a high dissolved oxygen concentration is fed to activated carbon, the dissolved oxygen concentration in the effluent water initially falls to 0.1 ppm or less, but then gradually rises as feeding is continued for a long time, usually for 1 hour to 5 days.

Water is usually fed to activated carbon at a space velocity of from 0.1 to 20 1/hr. Since it takes a long time for the dissolved oxygen concentration in the effluent to rise, the quantity of water to be used may be reduced by providing an oxygenating device and circulating water through activated carbon and the oxygenating device whereby oxygen is dissolved in water circulated from the activated carbon, and the water thus having an increased dissolved oxygen concentration is fed back to the activated carbon. In the oxygenating device, water is brought into contact with air or oxygen in order to absorb oxygen. Oxygen absorption (oxygenation) can be achieved by means of a generally employed device, or may be performed in a piping capable of contacting water with air or oxygen or within an apparatus for treating an aqueous acrylamide solution with activated carbon.

In the case of using pure water, which usually has a reduced dissolved oxygen concentration as low as 0.5 ppm after having been passed through a decarbonater, it should be contacted with air or oxygen in an oxygenating device so as to have an increased dissolved oxygen concentration.

The present invention is mainly applied to a fixed bed using granular activated carbon and may also be applicable to a fluidized bed using granular activated carbon. The present invention may further be applied to powdery activated carbon used in a fixed bed or other similar systems.

The present invention is suitable for purification of an aqueous acrylamide solution which does not contain a polymerization inhibitor, e.g., a copper ion, etc., and, in particular, an aqueous acrylamide solution obtained by a microbiological process. The present invention may also be applied to an aqueous acrylamide solution containing a cupric ion that is obtained by a catalytic hydration process. In this case, since there is no need to previously adsorb a copper ion onto activated carbon, the copper ion in the purified aqueous acrylamide solution can be reduced according to the method of the present invention.

According to the present invention, a purified aqueous acrylamide solution can be stably obtained while preventing incorporation of a polymer due to polymerization of acrylamide around activated carbon by contacting a crude aqueous acrylamide solution with activated carbon which has been contacted with water having a high concentration of dissolved oxygen.

When the present invention is applied to an aqueous acrylamide solution obtained by a microbiological process, the resulting purified acrylamide can be subjected to polymerization without any further treatment for removing copper ions, such as ion-exchanging, but replacement of oxygen in a polymerization system with nitrogen that is usually conducted before polymerization, to thereby produce an extremely high molecular weight polyacrylamide useful as a coagulant, etc. To the contrary, the conventional purification method involves adsorption of copper ions onto activated carbon prior to treatment, and thus requires removal of copper ions eluted out during the treatment from the treated aqueous acrylamide solution by, for example, ion-exchanging.

Further, the reducing property and oxygen adsorptivity of activated carbon vary depending on the kind thereof. According to the present invention, an aqueous acrylamide solution is fed to activated carbon after the activated carbon is treated with water having a high dissolved oxygen concentration until the dissolved oxygen concentration of the effluent water is increased to at least a desired predetermined level. Therefore, the dissolved oxygen concentration of the aqueous acrylamide solution passing through the activated carbon-packed bed can be maintained constant at said predetermined level or higher, and the acrylamide can be prevented from polymerization irrespective of the kind of activated carbon used.

The present invention is now illustrated in greater detail with reference to the following example. In the examples, all the parts and percents are by weight unless otherwise indicated.

EXAMPLE 1

A microorganism belonging to the genus Corynebacterium and capable of hydrating a nitrile, N-774 strain (FERM-P No. 4446), was aerobically cultivated in a medium (pH 7.2) containing 1% of glucose, 0.5% of peptone, 0.3% of yeast extract, 0.3% of malt extract and 0.05% of ferric sulfate heptahydrate. Forty parts of washed microbial cells collected from the culture (water content: 75%), 45 parts of acrylamide, 0.5 part of N,N'-methylenebisacrylamide and 40 parts of a 0.05M phosphoric acid buffer (pH 7.7) were mixed to form a uniform suspension. To the suspension were added 5 parts of a 5% aqueous solution of dimethylaminopropionitrile and 10 parts of a 2.5% potassium persulfate aqueous solution, and the resulting mixture was maintained at 10° C. for 30 minutes to effect polymerization. The resulting massive gel containing the microbial cells was crushed to small particles and thoroughly washed with a 0.05M phosphoric acid buffer (pH 7.7) to obtain 100 parts of the immobilized microbial cells.

Water and acrylonitrile were reacted at 0° C. in the presence of the above prepared immobilized microbial cells in a continuous reactor equipped with a stirrer to obtain a 20% aqueous solution of acrylamide. The resulting aqueous solution was found to contain 100 ppm of the unreacted acrylonitrile and not more than 0.02 ppm of a copper ion and have a chromaticity of about 6 APHA.

Separately, a glass-made column having an inner diameter of 60 mm and a length of 2 m was packed with 1,500 g of granular activated carbon ("Granular Shirasagi W 5C", a trade mark of product manufactured by Takeda Chemical Industries, Ltd.). A 1 liter-volume agitator and the column were connected by piping, and water was circulated therethrough at a rate of 8 l/hr by means of a pump, simultaneously with blowing air into the agitator. The dissolved oxygen concentration in the water running into the column was not less than 6 ppm, but that in the water effused from the column was not more than 0.1 ppm after ten hours from the start of circulation. Fifty-eight hours after the start of circulation, the dissolved oxygen concentration in the effluent had increased to 3 ppm.

At this point of time, the 20% aqueous solution of acrylamide as above obtained was passed through the column packed with activated carbon at a rate of 8 l/hr and discharged out of the system. The temperature of the aqueous solution was not higher than 10° C. When the aqueous acrylamide solution was fed over 12 days, the effluent had a chromaticity of about 1 APHA, and a polymer was noted in neither the column nor the effluent.

Confirmation of a polymer in the effluent was conducted by adding 100 ml of methanol to 10 ml of an effluent sample and examining whether white turbidity appeared.

COMPARATIVE EXAMPLE 1

The same procedures as described in Example 1 were repeated except that water having a dissolved oxygen concentration of 6 ppm or more was circulated for 16 hours (the dissolved oxygen concentration in the effluent water increased to 0.3 ppm) and at this point the aqueous acrylamide solution was fed to the column packed with activated carbon.

The effluent after 1 or 2 days from the start of the feeding was free from formation of a polymer, but that after 3 days became turbid immediately upon addition of methanol, indicating the presence of a polymer. Formation of a number of popcorn-shaped polymer particles was noted in the interior of the column of activated carbon, with a solution polymer being adhered to a part of said popcorn-shaped polymer particles.

While the invention has been described in detail and with reference to specific embodiments thereof, it will be apparent to one skilled in the art that various changes and modifications can be made therein without departing from the spirit and scope thereof.

What is claimed is:

1. A method for purifying an aqueous acrylamide soluton by using activated carbon, which comprises contacting activated carbon with water having oxygen dissolved therein at a concentration of at least 3 parts ppm at a space velocity of from 0.1 to 20 1/hr and until the dissolved oxygen concentration in the effluent water that has been contacted with the activated carbon increases to at least 0.5 ppm, and then contacting the aqueous acrylamide solution with the thus treated activated carbon.

2. A method as in claim 1, wherein the contacting between the activated carbon and water having oxygen dissolved therein is carried out by passing the water through a packed bed of activated carbon.

3. A method as in claim 1, wherein said water having oxygen dissolved therein has a dissolved oxygen concentration of at least 1 ppm.

4. A method as in claim 1, wherein the contacting between the activated carbon and water having oxygen dissolved therein is carried out until the dissolved oxygen concentration in the effluent water that has been contacted with the activated carbon increases to 1 ppm or more.

5. A method as in claim 1, wherein the aqueous acrylamide solution is obtained by using a microorganisms capable of hydrating a nitrile.

6. A method as in claim 2, wherein after the concentration of dissolved oxygen in the affluent water reaches at least 0.5 ppm the aqueous acrylamide solution is fed to packed bed of activated carbon.

7. A method as in claim 1, wherein said contacting is caried out for from one hour to five days.

8. A method as in claim 2, wherein said packed bed is a fixed bed.

9. A method as in claim 2, wherein said packed bed is a fluidized bed.

10. A method as in claim 2, wherein said activated carbon is granular activated carbon.

11. A method as in claim 1, wherein said aqueous acrylamide solution does not contain a a polymerization inhibitor.

12. A method as in claim 1, wherein said aqueous acrylamide solution does not contain copper ion.

13. A method as in claim 1, wherein said aquoues acrylamide solution contains cupric ion that is obtained by a catalytic hydration process.

14. A method as in claim 5, wherein said aqueous acrylamide solution is not subjected to treatment for removing copper ions.

15. A method for purifying an aqueous acrylamide solution by using activated carbon, which comprises contacting activated carbon with water having oxygen dissolved therein at a space velocity of from 0.1 to 20 1/hr, wherein the contacting between the activated carbon and water having oxygen dissolved therein is carried out by passing the water through a packed bed of activated carbon and wherein the effluent water that has been contacted with the activated carbon is passed through an oxygenating device wherein additional oxygen is dissolved in the water and the water having the thus increased dissolved oxygen concentration is contacted with the activated carbon until the dissolved oxygen concentration and the effluent water that has been contacted with the activated carbon increases to at least 0.5 ppm, and then contacting the aqueous acrylamide solution with the thus treated activated carbon.

* * * * *